US012653382B2

(12) United States Patent
Gane et al.

(10) Patent No.: US 12,653,382 B2
(45) Date of Patent: Jun. 16, 2026

(54) SYSTEMS AND METHODS FOR CONTROLLING AUTOFOCUS OPERATIONS

(71) Applicant: SYNAPTIVE MEDICAL INC., Toronto (CA)

(72) Inventors: Luke William Gane, Toronto (CA); David Bruce Gallop, Toronto (CA)

(73) Assignee: SYNAPTIVE MEDICAL INC.

( * ) Notice: Subject to any disclaimer, the term of this patent is extended or adjusted under 35 U.S.C. 154(b) by 518 days.

(21) Appl. No.: 18/189,303

(22) Filed: Mar. 24, 2023

(65) Prior Publication Data

US 2023/0225594 A1     Jul. 20, 2023

Related U.S. Application Data

(63) Continuation of application No. 16/655,779, filed on Oct. 17, 2019, now Pat. No. 11,627,868.

(51) Int. Cl.
| | |
|---|---|
| *A61B 1/00* | (2006.01) |
| *A61B 34/35* | (2016.01) |
| *A61B 90/00* | (2016.01) |

(52) U.S. Cl.
CPC .......... *A61B 1/00188* (2013.01); *A61B 34/35* (2016.02); *A61B 90/361* (2016.02); *A61B 1/00193* (2013.01)

(58) Field of Classification Search
CPC ... A61B 1/00188; A61B 34/35; A61B 90/361;
A61B 1/00193; A61B 2034/2065; A61B 2034/2051; A61B 2090/365; A61B 2034/2055; A61B 1/00006; A61B 2034/2057; H04N 23/60; H04N 23/67
See application file for complete search history.

(56) References Cited

U.S. PATENT DOCUMENTS

| | | | | |
|---|---|---|---|---|
| 9,718,190 B2 * | 8/2017 | Larkin | ................... | B25J 9/1694 |
| 9,827,054 B2 * | 11/2017 | Richmond | ............. | G16H 40/63 |
| 2014/0111628 A1 * | 4/2014 | Yoshino | ................... | A61B 1/05 |
| | | | | 348/65 |
| 2014/0163359 A1 * | 6/2014 | Sholev | ............... | A61B 1/00011 |
| | | | | 600/407 |
| 2018/0289428 A1 * | 10/2018 | Lee | ...................... | G02B 21/365 |

* cited by examiner

*Primary Examiner* — Niketa Patel
*Assistant Examiner* — Karmel J Webster

(57) ABSTRACT

A method for performing auto-focus in a camera is disclosed. The method includes: receiving, from a tracking system for tracking a position of a medical instrument, a signal; determining, based on the received signal, that the medical instrument is removed from a field of view of the camera; in response to determining that a continuous auto-focus mode for the camera is enabled: retrieving, from a database, a first focus distance value representing a focus distance that was most recently set with intent for the camera; and automatically updating a focus distance of the camera to the first focus distance value.

20 Claims, 9 Drawing Sheets

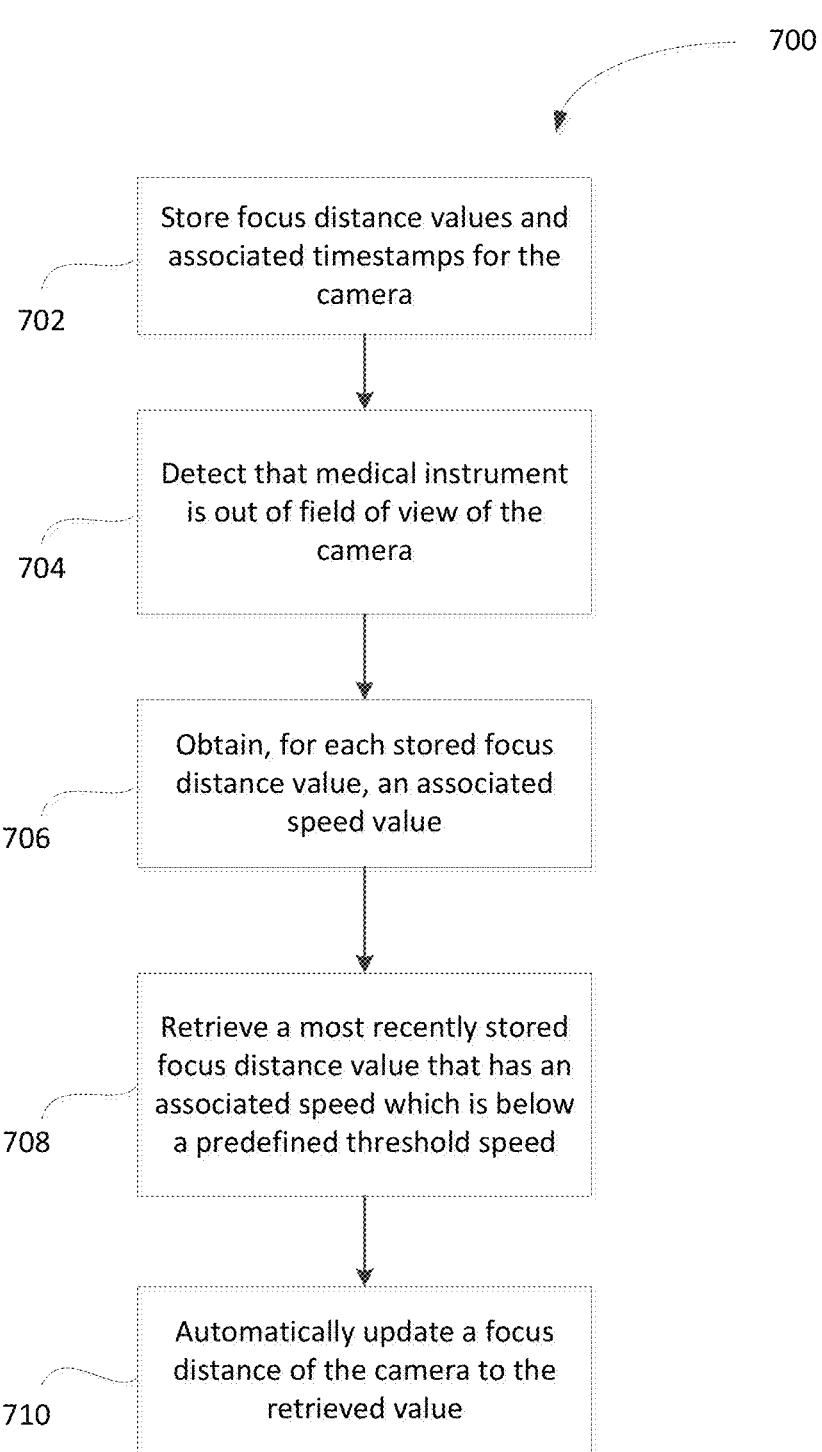

700

Store focus distance values and associated timestamps for the camera

702

Detect that medical instrument is out of field of view of the camera

704

Obtain, for each stored focus distance value, an associated speed value

706

Retrieve a most recently stored focus distance value that has an associated speed which is below a predefined threshold speed

708

Automatically update a focus distance of the camera to the retrieved value

SYSTEMS AND METHODS FOR CONTROLLING AUTOFOCUS OPERATIONS

CROSS REFERENCE TO RELATED APPLICATIONS

The application claims priority to and the benefit of U.S. Utility patent application Ser. No. 16/655,779, entitled "SYSTEMS AND METHODS FOR CONTROLLING AUTO-FOCUS OPERATIONS", filed on Oct. 17, 2019, the disclosure of which are incorporated herein by reference in their entirety.

TECHNICAL FIELD

The present disclosure relates to medical imaging and, in particular, to optical imaging systems suitable for use in image-guided medical procedures.

BACKGROUND

Digital microscopes support advanced visualization during medical procedures. For example, digital surgical microscopes provide magnified views of anatomical structures during a surgery. Digital microscopes use optics and digital (e.g., CCD-based) cameras to capture images in real-time and output the images to displays for viewing by a surgeon, operator, etc.

In image-guided medical applications, such as surgery or diagnostic imaging, accurate three-dimensional (3-D) visualization of patient anatomy and surgical tools is crucial. A medical navigation system is often used to support image-guided surgery. In an exemplary medical navigation system, an optical imaging system may be provided for generating 3-D views of a surgical site. A positioning system, such as a mechanical arm, may support the optical imaging system and facilitate maneuvering the optical imaging system to an appropriate position and orientation to maintain alignment with a viewing target.

The optical imaging system may be adapted to perform auto-focus, which enables a camera of the optical imaging system to automatically focus on a defined viewing target, such as a tracked medical instrument. Continuous auto-focus maintains the viewing target constantly in focus. In particular, auto-focus operations dynamically focus the image on the viewing target, enabling an operator (e.g., surgeon) to control focus during a medical procedure without having to manually adjust the focus optics. By virtue of the auto-focus functionality, the operator may observe a surgical site of interest using the camera by moving the viewing target over, or in proximity of, the surgical site.

Continuous auto-focus may be disrupted, for example, by actions of the operator or unintended changes to the viewing target. For example, if the viewing target leaves a field of view of the camera, an out-of-focus image may be produced by the camera. Even a momentary loss of focus of the optical imaging system may lead to serious consequences in a medical procedure. It is desirable to mitigate the disruptive effects resulting from loss of continuous auto-focus during a medical procedure.

BRIEF DESCRIPTION OF DRAWINGS

Reference will now be made, by way of example, to the accompanying drawings which show example embodiments of the present application and in which:

FIG. 7 shows, in flowchart form, another example method for performing auto-focus in a camera of the optical imaging system of FIG. 5.

Like reference numerals are used in the drawings to denote like elements and features.

DETAILED DESCRIPTION OF EXAMPLE EMBODIMENTS

Figure 1:
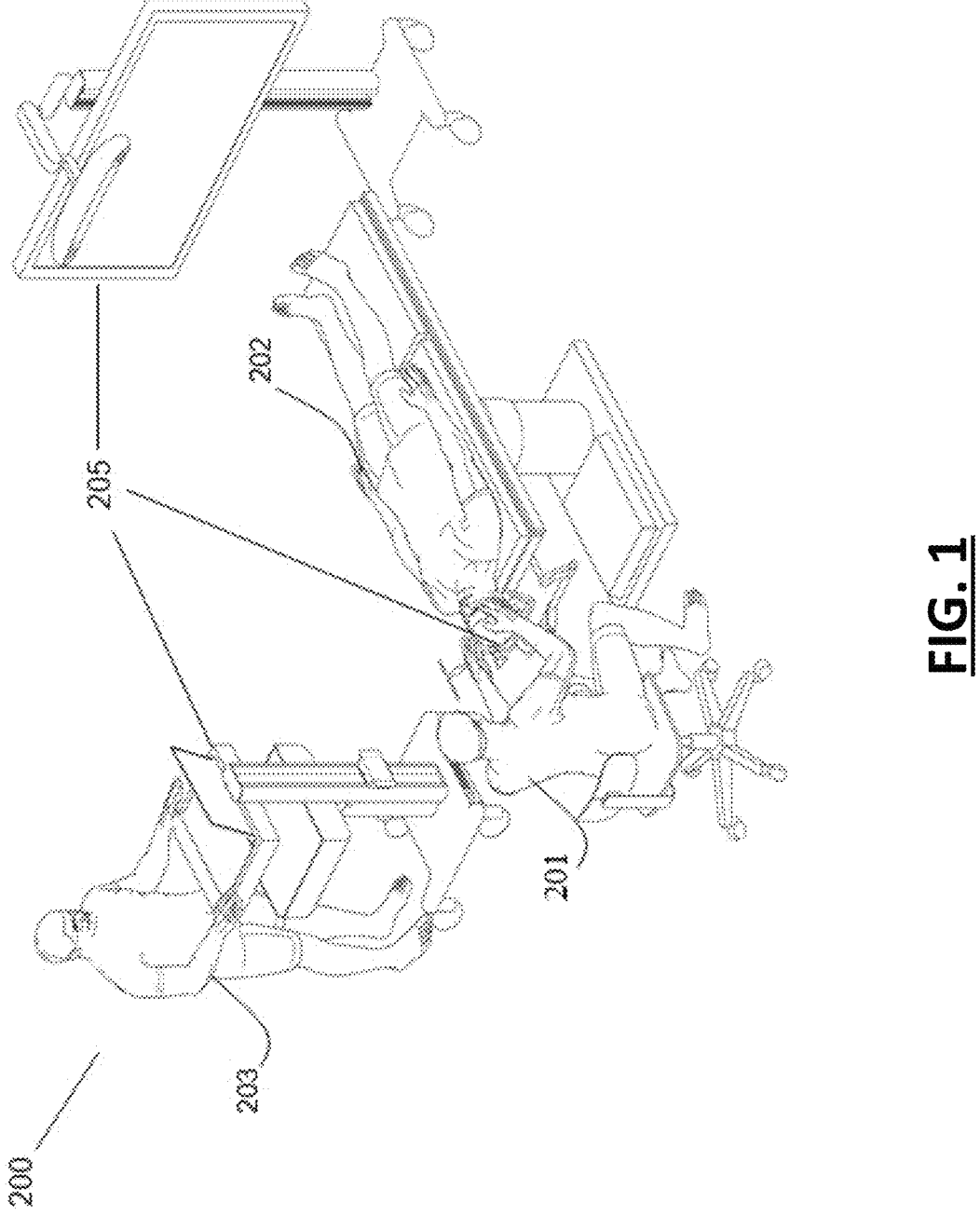
FIG. 1 shows an example medical navigation system to support image-guided surgery.

In one aspect, the present disclosure describes a processor-implemented method for performing auto-focus in a camera. The method includes: receiving, from a tracking system for tracking a position of a medical instrument, a signal; determining, based on the received signal, that the medical instrument is removed from a field of view of the camera; in response to determining that a continuous auto-focus mode for the camera is enabled: retrieving, from a database, a first focus distance value representing a focus distance that was most recently set with intent for the camera; and automatically updating a focus distance of the camera to the first focus distance value.

In some implementations, the method may further comprise storing, in the database, a predetermined number of most recent focus distance values for the camera and time-stamps associated with the focus distance values.

In some implementations, retrieving the first focus distance value may comprise: obtaining, for each focus distance value stored in the database, an associated speed value, the associated speed value representing an approximate speed of a tracked point of the medical instrument at the focus distance; retrieving, from the database, a most recently stored focus distance value having an associated speed that is below a predefined threshold speed.

In some implementations, the associated speed may be obtained based on a finite difference computation using focus distance values stored in the database.

In some implementations, the predefined threshold speed may be 0.1 meter per second.

In some implementations, the camera may be configured to automatically focus to a predetermined point relative to the medical instrument.

In some implementations, the continuous auto-focus mode may be activated via a voice input or activation of a foot pedal.

In some implementations, detecting that the medical instrument is removed from the field of view of the camera may comprise determining that the predetermined point is no longer within the field of view of the camera.

In some implementations, detecting that the medical instrument is removed from the field of view of the camera may comprise determining that an approximate speed of the medical instrument exceeds a predefined threshold speed.

In some implementations, the method may further comprise computing a speed curve representing approximate speeds of the medical instrument which are associated with the stored focus distance values.

In another aspect, the present disclosure describes a medical navigation system to support a medical procedure. The medical navigation system includes a tracking system for tracking a position of a medical instrument, a surgical camera for imaging a target surgical site, and a processor coupled to the tracking system and the surgical camera. The processor is configured to: determine, based on a signal from the tracking system, that the medical instrument is removed from a field of view of the surgical camera; in response to determining that a continuous auto-focus mode for the surgical camera is enabled: retrieve, from a database, a first focus distance value representing a focus distance that was most recently set with intent for the surgical camera; and automatically update a focus distance of the surgical camera to the first focus distance value.

In yet another aspect, the present disclosure describes an optical imaging system for imaging a target during a medical procedure. The optical imaging system includes a movable arm, a camera mounted on the movable arm, the camera capturing images of a target surgical site, and a processor for calibrating the camera. The processor is configured to: receive, from a tracking system for tracking a position of a medical instrument, a signal; determine, based on the received signal, that the medical instrument is removed from a field of view of the camera; in response to determining that a continuous auto-focus mode for the camera is enabled: retrieve, from a database, a first focus distance value representing a focus distance that was most recently set with intent for the camera; and automatically update a focus distance of the camera to the first focus distance value.

Other example embodiments of the present disclosure will be apparent to those of ordinary skill in the art from a review of the following detailed descriptions in conjunction with the drawings.

In the present application, the phrase "access port" is intended to refer to a cannula, a conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

In the present application, the term "intraoperative" is intended to refer to an action, process, method, event, or step that occurs or is carried out during at least a portion of a medical procedure. Intraoperative, as defined herein, is not limited to surgical procedures, and may refer to other types of medical procedures, such as diagnostic and therapeutic procedures.

In the present application, the term "and/or" is intended to cover all possible combinations and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

A medical navigation system may be configured to support image-guided medical procedures. The medical navigation system may include a tracking system for tracking one or more medical instruments and an optical imaging system. The optical imaging system includes a camera for imaging a surgical site of interest during a medical procedure. The optical imaging system may be configured to perform auto-focusing relative to a tracked tool that is used in a medical procedure. The position and orientation of a tracked tool may be determined by the tracking system, and a controller of the optical imaging system may perform auto-focusing to focus the captured image on a point defined relative to the tracked tool. By moving the tracked tool over, or in proximity to, a target surgical site, the operator of the medical navigation system (e.g. a surgeon) may be able to observe the surgical site without manually controlling focus optics of the optical imaging system.

"Continuous" auto-focus maintains a viewing target, such as a moving object, constantly in focus. A continuous auto-focus mode for a medical navigation system may allow a tracked tool (e.g. a medical instrument) to be automatically kept in focus of a camera of the optical imaging system. This auto-focus behavior may be disrupted, for example, when the tracked tool is removed from a field of view of the camera. If the camera loses focus, an out-of-focus image may be produced by the camera, and the operator's ability to observe the target surgical site using the camera may be impeded.

The present application discloses improved auto-focusing capabilities of an optical imaging system of a medical navigation system. A controller of the optical imaging system is configured to perform operations for recovering continuous auto-focus for a camera of the optical imaging system. The controller receives a signal from the tracking system indicating a position and/or orientation of the target tool relative to the camera. The controller determines, based on the received signal, that the target tool is removed from a field of view of the camera. If continuous auto-focus mode is enabled for the camera, the controller is configured to retrieve, from a database, a first focus distance value representing a focus distance that was most recently set with intent for the camera. The focus distance of the camera may then be automatically updated to the retrieved first focus distance value.

Reference is first made to FIG. 1, which shows an example medical navigation system 200. The example medical navigation system 200 may be used to support image-guided surgery. As shown in FIG. 1, a surgeon 201 performs surgery on a patient 202 in an operating room environment. A medical navigation system 205 may include an equipment tower, tracking system, displays, and tracked instruments to assist the surgeon 201 during a procedure. An operator 203 may also be present to operate, control, and provide assistance for the medical navigation system 205.

Figure 2:
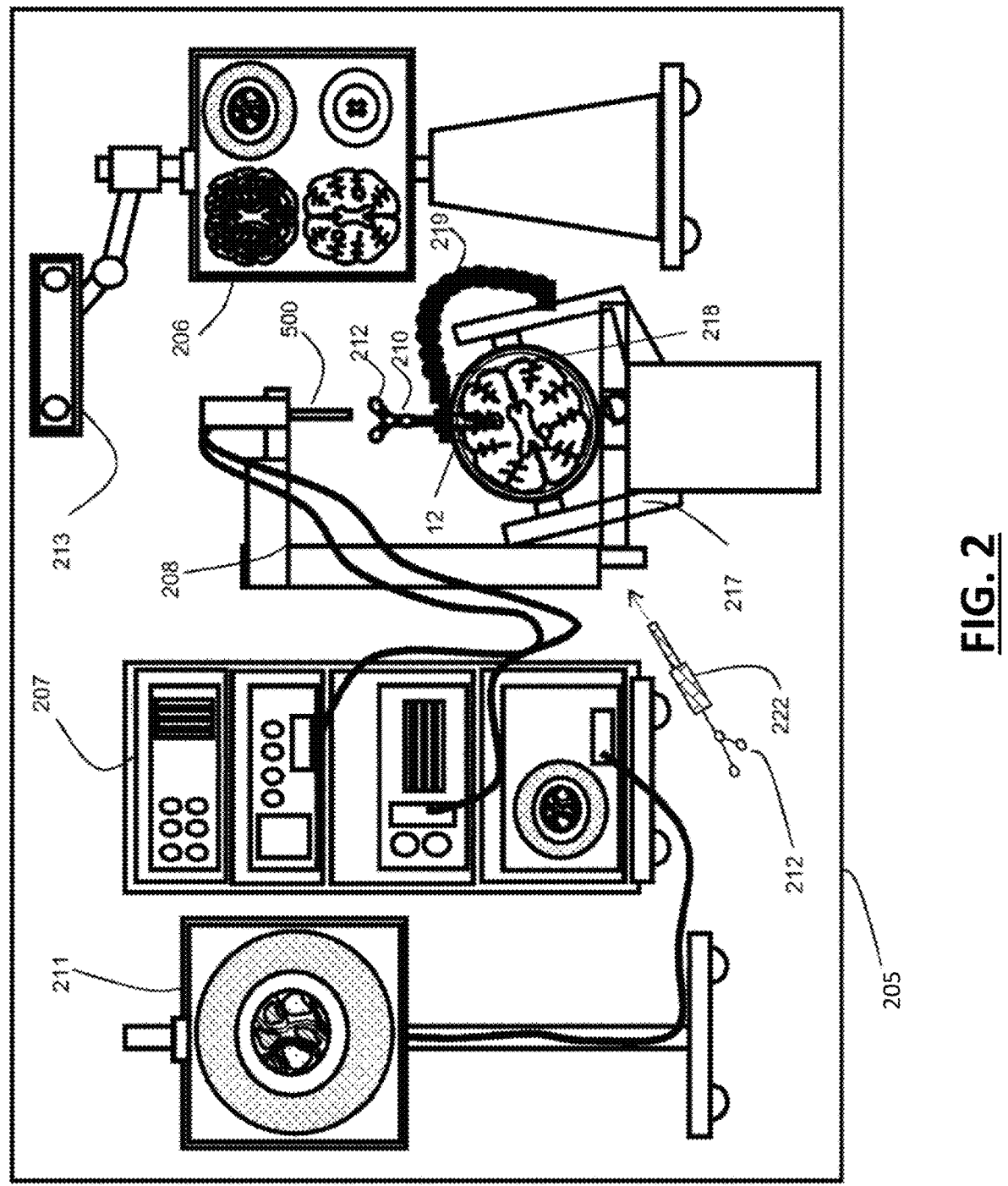
FIG. 2 illustrates components of an example medical navigation system.

FIG. 2 shows components of an example medical navigation system 205. The disclosed optical imaging system may be used in the context of the medical navigation system 205. The medical navigation system 205 may include one or more displays 206, 211 for displaying video images, an equipment tower 207, and a positioning system 208, such as a medical arm, which may support an optical imaging system 500. One or more of the displays 206, 211 may include a touch-sensitive display for receiving touch input. The equipment tower 207 may be mounted on a frame, such as a rack or cart, and may contain a power supply and a computer/controller that may execute planning software, navigation software, and/or other software to manage the positioning system 208. In some embodiments, the equipment tower 207 may be a single tower configuration operating with dual displays 206, 211; however, other configurations (e.g. dual tower, single display etc.) may be possible. The equipment tower 207 may also be configured with a universal power supply (UPS) to provide for emergency power, in addition to a regular AC adapter power supply.

A portion of the patient's anatomy may be held in place by a holder. For example, as shown in FIG. 2, the patient's head and brain may be held in place by a head holder 217. An access port 12 and associated introducer 210 may be inserted into the head, to provide access to a surgical site in the head. The optical imaging system 500 may be used to view down the access port 12 at a sufficient magnification to allow for enhanced visibility. The output of the optical imaging system 500 may be received by one or more computers or controllers to generate a view that may be depicted on a visual display (e.g. one or more of displays 206, 211).

In some embodiments, the medical navigation system 205 may include a tracked pointer 222. The tracked pointer 222, which may include markers 212 to enable tracking by a tracking camera 213, may be used to identify points (e.g. fiducial points) on a patient. An operator, typically a nurse or the surgeon 201, may use the tracked pointer 222 to identify the location of points on the patient 202, in order to register the location of selected points on the patient 202 in the medical navigation system 205. In some embodiments, a guided robotic system with closed loop control may be used as a proxy for human interaction. Guidance to the robotic system may be provided by any combination of input sources such as image analysis, tracking of objects in the operating room using markers placed on various objects of interest, or any other suitable robotic system guidance techniques.

Fiducial markers 212 may be connected to the introducer 210 for tracking by the tracking camera 213, which may provide positional information of the introducer 210 from the medical navigation system 205. In some embodiments, the fiducial markers 212 may be alternatively or additionally attached to the access port 12. In some embodiments, the tracking camera 213 may be a 3-D infrared optical tracking stereo camera. In some other examples, the tracking camera 213 may be an electromagnetic system (not shown), such as a field transmitter, that is configured to use at least one receiver coil disposed in relation to the tool(s) intended for tracking. A known profile of the electromagnetic field and known position of receiver coil(s) relative to each other may be used to infer the location of the tracked tool(s) using the induced signals and their phases in each of the receiver coils.

Location data of the positioning system 208 and/or access port 12 may be determined by the tracking camera 213 by detection of the fiducial markers 212 placed on or otherwise in fixed relation (e.g. in rigid connection) to any of the positioning system 208, the access port 12, the introducer 210, the tracked pointer 222 and/or other tracked instruments. The fiducial marker(s) 212 may be active or passive markers. The displays 206, 2011 may provide an output of the computed data of the medical navigation system 205. In some embodiments, the output provided by the displays 206, 211 may include at least one of axial, sagittal, or coronal views of patient anatomy as part of a multi-view output.

The active or passive fiducial markers 212 may be placed on tools (e.g. the access port 12 and/or the optical imaging system 500) to be tracked, to determine the location and orientation of these tools using the tracking camera 213 and medical navigation system 205. A stereo camera of the tracking system may be configured to detect the fiducial markers 212 and to capture images thereof for providing identifiable points for tracking the tools. A tracked tool may be defined by a grouping of markers 212, whereby a rigid body may be defined and identified by the tracking system. This may, in turn, be used to determine the position and/or orientation in three dimensions of a tracked tool in a virtual space. The position and orientation of the tracked tool in 3-D may be tracked in six degrees of freedom (e.g. x, y, z coordinates and pitch, yaw, roll rotations), in five degrees of freedom (e.g. x, y, z coordinates and two degrees of free rotation), and preferably tracked in at least three degrees of freedom (e.g. tracking the position of the tip of a tool in at least x, y, z coordinates). In typical use with medical navigation systems, at least three markers 212 are provided on a tracked tool to define the tool in virtual space; however, it is known to be advantageous for four or more markers 212 to be used.

Camera images capturing the markers 212 may be logged and tracked by, for example, a closed-circuit television (CCTV) camera. The markers 212 may be selectable to enable, assist or facilitate in segmentation of the captured images. For example, infrared (IR)-reflecting markers and an IR light source from the direction of the camera may be used. In some embodiments, the spatial position and orientation of the tracked tool and/or the actual and desired position and orientation of the positioning system 208 may be determined by optical detection using a camera. The optical detection may be performed using an optical camera, rendering the markers 212 optically visible.

In some embodiments, the markers 212 (e.g. reflectospheres) may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the medical navigation system 205. The individual identifiers may provide information to the medical navigation system 205, such as information relating to the size and/or shape of the tool within the medical navigation system 205. The identifier may also provide additional information, such as the tool's central point or the tool's central axis, among other information. The virtual tool may also be determined from a database of tools stored in, or provided to, the medical navigation system 205. The markers 212 may be tracked relative to a reference point, or a reference object, in the operating room, such as the patient 202.

Various types of fiducial markers may be used. The markers 212 may comprise the same type or a combination of at least two different types. Possible types of markers include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools to which such markers are attached. Reflective adhesives, structures and patterns, glass markers, and LED markers may be detectable using optical detectors, while RF and EM markers may be detectable using antennas. Different marker types may be selected to suit different operating conditions.

In some embodiments, the markers 212 may include printed or 3-D designs that may be used for detection by an auxiliary camera, such as a wide-field camera (not shown) and/or the optical imaging system 500. Printed markers may also be used as a calibration pattern, for example, to provide distance information (e.g. 3-D distance information) to an optical detector. Printed identification markers may include designs such as concentric circles with different ring spacing and/or different types of bar codes, among other designs. In some embodiments, in addition to or in place of using markers 212, the contours of known objects (e.g. the side of the access port 12) could be captured by and identified using optical imaging devices and the tracking system.

A guide clamp 218 (or more generally a guide) for holding the access port 12 may be provided in the medical navigation system 205. The guide clamp 218 may allow the access port 12 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g. on another patient support, such as on the surgical bed), to ensure that when locked in place, the guide clamp 218 does not move relative to the patient's head.

In a surgical operating room/theatre, setup of a medical navigation system may be complicated; numerous pieces of equipment associated with the surgical procedure, as well as various elements of the medical navigation system 205, may need to be arranged and prepared. Setup time typically increases as more equipment is added. To assist in addressing this, the medical navigation system 205 may include two additional wide-field cameras to enable video overlay information. Video overlay information can be inserted into displayed images, such as images displayed on one or more of the displays 206, 211. The overlay information may illustrate the physical space where accuracy of the 3-D tracking system (which is typically part of the medical navigation system 205) is greater, may illustrate the available range of motion of the positioning system 208 and/or the optical imaging system 500, and may help to guide head and/or patient positioning.

The medical navigation system 205 may provide tools to the surgeon that may help to provide more relevant information to the surgeon, and may assist in improving performance and accuracy of port-based surgical operations. Although described in the present disclosure in the context of port-based neurosurgery (e.g. for removal of brain tumors and/or for treatment of intracranial hemorrhages (ICH)), the medical navigation system 205 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same medical navigation system 205 may be used for carrying out any or all of these procedures, with or without modification as appropriate.

In some embodiments, the tracking camera 213 may be part of a suitable tracking system. In some embodiments, the tracking camera 213 (and any associated tracking system that uses the tracking camera 213) may be replaced with a suitable tracking system which may or may not use camera-based tracking techniques. For example, a tracking system that does not use the tracking camera 213, such as a radiofrequency tracking system, may be used with the medical navigation system 205.

Figure 3:
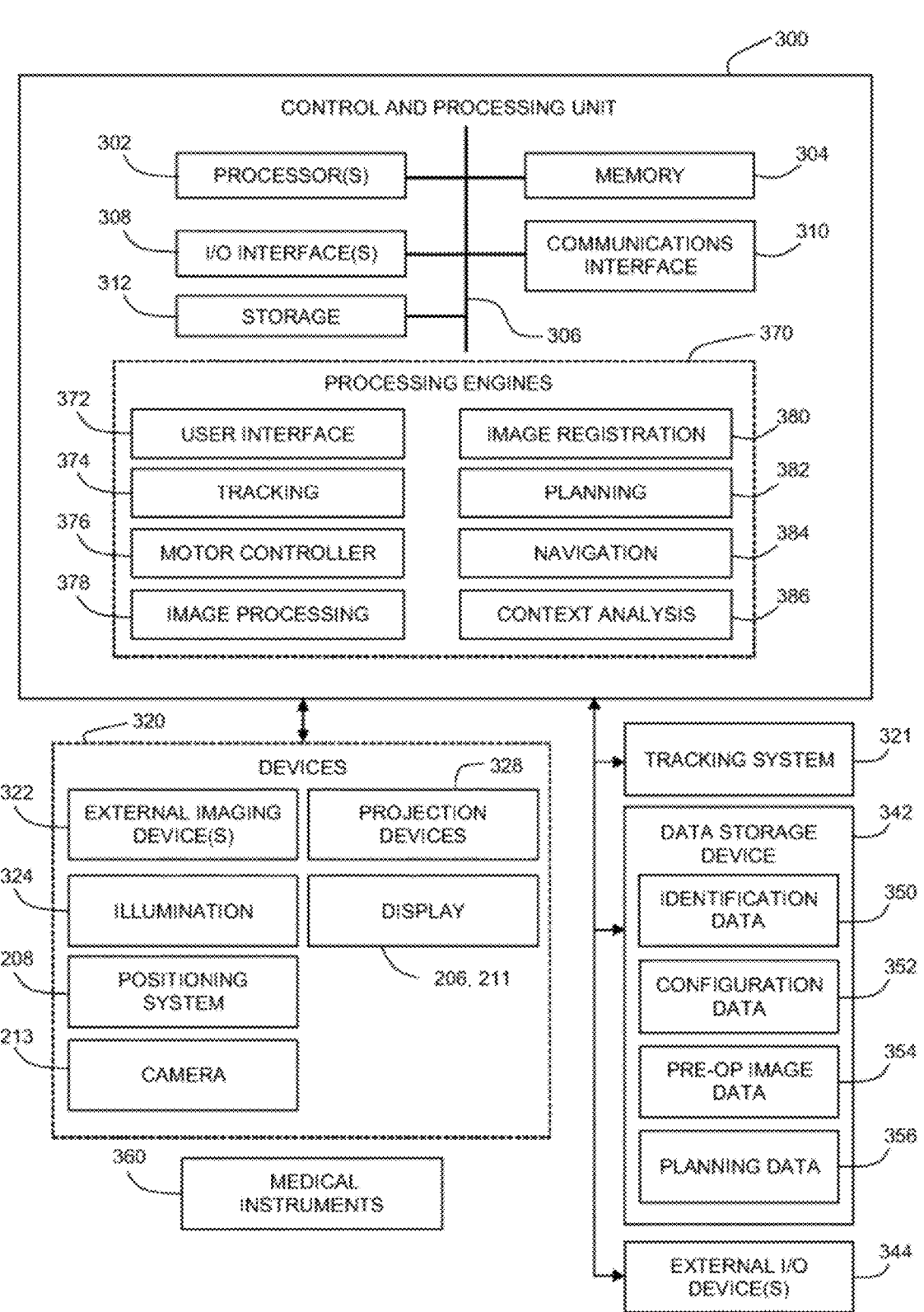
FIG. 3 is a block diagram illustrating an example control and processing system which may be used in the example medical navigation system of FIGS. 1 and 2.

FIG. 3 is a block diagram illustrating an example control and processing system 300 that may be used as part of the medical navigation system 205 shown in FIG. 2 (e.g. as part of the equipment tower 207). As shown in FIG. 3, the control and processing system 300 may include one or more processors 302, a memory 304, a system bus 306, one or more input/output interfaces 308, a communications interface 310, and storage device 312. The control and processing system 300 may interface with other external devices, such as a tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. The data storage device 342 may also include preoperative image data 354 and/or medical procedure planning data 356. Although the data storage device 342 is shown as a single device in FIG. 3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The tracking system 321 may be employed to track one or more medical instruments 360 and spatially register the one or more tracked medical instruments to an intraoperative reference frame. For example, a medical instrument 360 may include tracking markers such as tracking spheres that may be recognizable by the tracking camera 213. In one example, the tracking camera 213 may be an infrared (IR) tracking camera. In another example, a sheath placed over a medical instrument 360 may be connected to and controlled by the control and processing unit 300.

The control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, the positioning system 208, the tracking camera 213, one or more projection devices 328, and one or more displays 206, 211.

Exemplary aspects of the disclosure can be implemented via the processor(s) 302 and/or memory 304. For example, the functionalities described herein can be partially implemented via hardware logic in the processor 302 and partially using the instructions stored in the memory 304, as at least one processing module or engine 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in some embodiments, the processing modules 370 may be stored in the memory 304 and the processing modules 370 may be collectively referred to as processing modules 370. In some embodiments, two or more modules 370 may be used together to perform a function. Although depicted as separate modules 370, the modules 370 may be embodied as a unified set of computer-readable instructions (e.g. stored in the memory 304) rather than distinct sets of instructions.

Figure 4A:
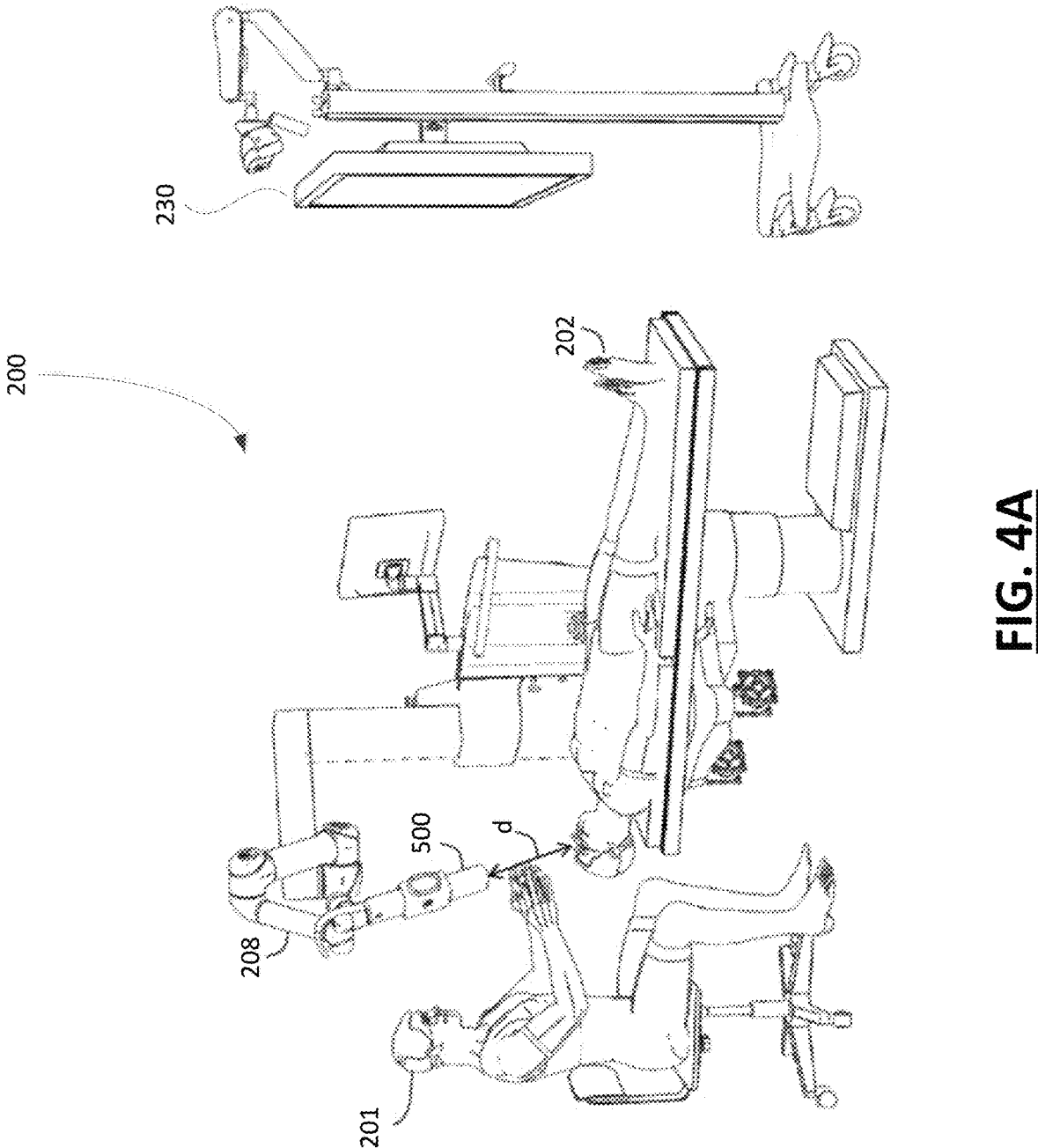
FIG. 4A shows the use of an example optical imaging system during a medical procedure.

FIG. 4A illustrates use of an example optical imaging system 500, described further below, in a medical procedure. Although FIG. 4A shows the optical imaging system 500 being used in the context of a navigation system environment 200 (e.g. using a medical navigation system as described above), the optical imaging system 500 may also be used outside of a navigation system environment.

An operator, typically a surgeon 201, may use the optical imaging system 500 to observe a surgical site (e.g. to look down an access port). The optical imaging system 500 may be attached to a positioning system 208, such as a controllable and adjustable robotic arm. The position and orientation of the positioning system 208, imaging system 500, and/or access port may be tracked using a tracking system, such as described above for the medical navigation system 205. The distance between the optical imaging system 500 (more specifically, the aperture of the optical imaging system 500) and the viewing target may be referred to as the working distance. The optical imaging system 500 may be designed to be used in a predefined range of working distance (e.g. in the range of between 15 and 75 centimeters). It should be noted that, if the optical imaging system 500 is mounted on the positioning system 208, the actual available range of working distance may be dependent on both the working distance of the optical imaging system 500 as well as the workspace and kinematics of the positioning system 208. In some embodiments, the optical imaging system 500 may include a manual release button that, when actuated, enables the optical imaging system to be positioned manually. For example, the controller of the optical imaging system 500 may be responsive to manual control input received via a user interface.

Figure 5:
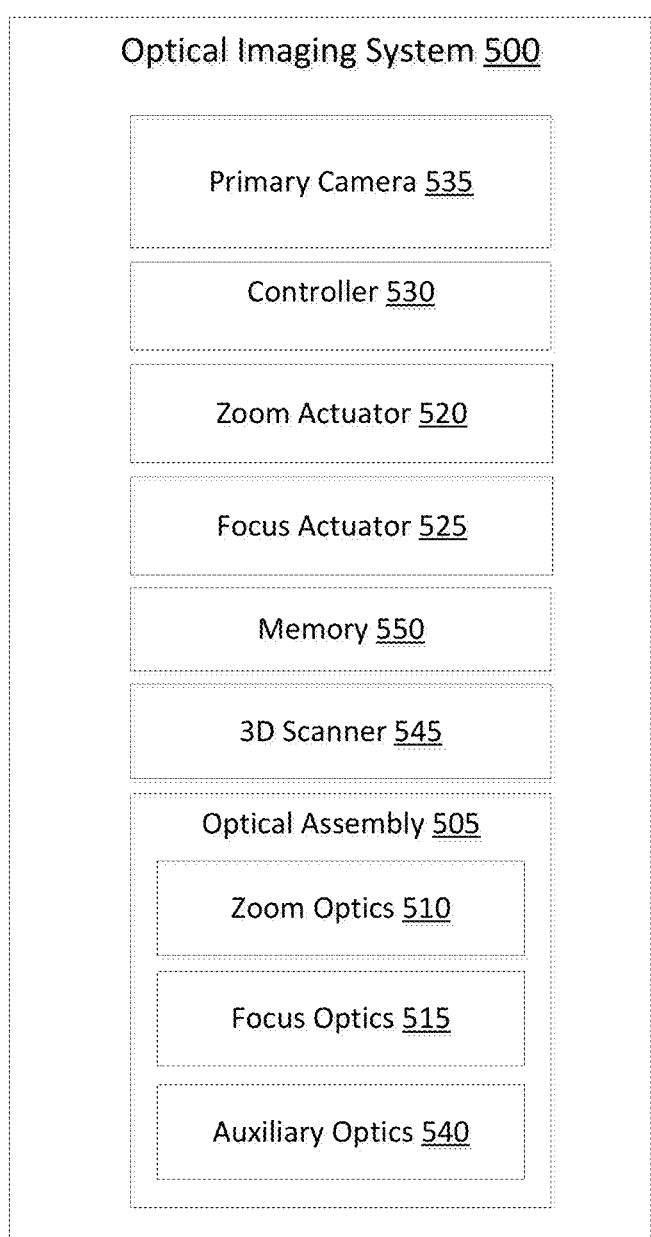
FIG. 5 is a block diagram illustrating components of an example optical imaging system 500.

Reference is made to FIG. 5, which illustrates components of an example optical imaging system 500. The optical imaging system 500 includes an optical assembly 505 (which may also be referred to as an optical train). The optical assembly 505 includes optics, e.g. lenses, optical fibers, etc., for focusing and zooming on a viewing target. Specifically, the optical assembly 505 includes zoom optics 510 (which may include one or more zoom lenses) and focus optics 515 (which may include one or more focus lenses). Each of the zoom optics 510 and the focus optics 515 may be independently movable within the optical assembly 505 for respectively adjusting the zoom and focus. Where the zoom optics 510 and/or the focus optics 515 include more than one lens, each individual lens may be independently movable. The optical assembly 505 may comprise an aperture (not shown) which is adjustable.

The optical imaging system 500 may also include a zoom actuator 520 and a focus actuator 525 for respectively positioning the zoom optics 510 and the focus optics 515. The zoom actuator 520 and/or the focus actuator 525 may comprise electric motors or other types of actuators, such as pneumatic actuators, hydraulic actuators, shape-changing materials, e.g., piezoelectric materials or other smart materials, or engines, among other possibilities. Although the zoom actuator 520 and the focus actuator 525 are shown outside of the optical assembly 505, in some embodiments, the zoom actuator 520 and the focus actuator 525 are components of, or are integrated with, the optical assembly 505. The zoom actuator 520 and the focus actuator 525 may operate independently, to respectively control positioning of the zoom optics 510 and the focus optics 515. The lens(es) of the zoom optics 510 and/or the focus optics 515 may each be mounted on a linear stage, e.g. a motion system that restricts an object to move in a single axis, which may include a linear guide and an actuator, or a conveyor system such as a conveyor belt mechanism that is respectively moved by the zoom actuator 520 and/or the focus actuator 525 to control positioning of the zoom optics 510 and/or the focus optics 515. In some embodiments, the zoom optics 510 may be mounted on a linear stage that is driven, via a belt drive, by the zoom actuator 520, while the focus optics 515 may be geared to the focus actuator 525. The independent operation of the zoom actuator 520 and the focus actuator 525 may enable the zoom and focus to be adjusted independently. Thus, when an image is in focus, the zoom may be adjusted without requiring further adjustments to the focus optics 515 to produce a focused image.

Operation of the zoom actuator 520 and the focus actuator 525 may be controlled by a controller 530 (e.g. a microprocessor) of the optical imaging system 500. The controller 530 may receive control input from an external system, such as an external processor or an input device. The control input may indicate a desired zoom/focus, and the controller 530 may, in response, cause the zoom actuator 520 or the focus actuator 525 to move the zoom optics 510 or the focus optics 515 accordingly, to achieve the desired zoom/focus. In some embodiments, the zoom optics 510 and/or the focus optics 515 may be moved or actuated without the use of the zoom actuator 520 and/or the focus actuator 525. For example, the focus optics 515 may use electrically-tunable lenses or other deformable material that is directly controlled by the controller 530.

The optical imaging system 500 may enable an operator (e.g. a surgeon) of the medical navigation system 205 to control zoom or focus during a medical procedure without having to manually adjust the zoom optics 510 or focus optics 515. For example, the operator may provide control input to the controller 530 verbally, e.g. via a voice recognition input system, by instructing an assistant to enter control input into an external input device, via a user interface provided by a workstation, using a foot pedal, or by other such means. In some embodiments, the controller 530 may execute preset instructions to maintain the zoom and/or focus at preset values, for example, to perform auto-focusing, without requiring further control input during a medical procedure.

An external processor (e.g. a processor of a workstation or the medical navigation system 205) in communication with the controller 530 may be used to provide control input to the controller 530. For example, the external processor may provide a graphical user interface for receiving input instructions to control zoom and/or focus of the optical imaging system 500. The controller 530 may alternatively or additionally be in communication with an external input system, e.g., a voice-recognition input system or a foot pedal. The optical assembly 505 includes at least one auxiliary optic 540, e.g., an adjustable aperture, which is static or dynamic. Where the auxiliary optics 540 is dynamic, the auxiliary optics 540 may be moved using an auxiliary actuator (not shown) which is controlled by the controller 530.

The optical imaging system 500 includes a camera 535 (or video-scope) that is configured to capture image data from the optical assembly 505. Operation of the camera may be controlled by the controller 530. The camera 535 may also output data to an external system, such as an external workstation or external output device, to view the captured image data. In some embodiments, the camera 535 outputs data to the controller 530, which, in turn, transmits the data to an external system for viewing. The captured images may be viewable on a larger display and may be displayed together with other information relevant to a medical procedure, e.g. a wide-field view of the surgical site, navigation markers, 3D images, etc. Image data captured by the camera 535 may be displayed on a display together with a wide-field view of the surgical site, for example, in a multiple-view user interface. The portion of the surgical site that is captured by the camera 535 may be visually indicated in the wide-field view of the surgical site.

The optical imaging system 500 may include a three-dimensional (3-D) scanner 545 or 3-D camera for obtaining 3-D information of a viewing target. 3-D Information from the 3-D scanner 545 may be captured by the camera 535, or captured by the 3D scanner 545 itself. Operation of the 3-D scanner 545 may be controlled by the controller 530, and the 3-D scanner 545 may transmit data to the controller 530. 3-D information from the 3-D scanner 545 may be used to generate a 3-D image of a viewing target (e.g. a 3-D image of a target tumor to be re-seated). 3-D information may also be useful in an augmented reality (AR) display provided by an external system. For example, an AR display may, using information from a navigation system to register 3-D information with optical images, overlay a 3-D image of a target specimen on a real-time optical image captured by the camera 535.

The controller 530 is coupled to a memory 550. The memory 550 may be internal or external in relation to the optical imaging system 500. Data received by the controller 530 (e.g. image data from the camera 535, 3-D data from the 3D scanner, etc.) may be stored in the memory 550. The memory 550 may also contain instructions to enable the controller to operate the zoom actuator 520 and the focus actuator 525. For example, the memory 550 may store instructions to enable the controller 530 to perform auto-focusing. The optical imaging system 500 may communicate with an external system, such as a navigation system or a workstation, via wired or wireless communication. In some embodiments, the optical imaging system 500 may include a wireless transceiver (not shown) to enable wireless communication. In some embodiments, the optical imaging system 500 includes a power source (e.g. a battery) or a connector to a power source, such as an AC adaptor. The optical imaging system 500 may receive power via a connection to an external system, such as an external workstation or processor.

In some embodiments, the optical assembly 505, zoom actuator 520, focus actuator 525, and camera 535 may all be housed within a single housing (not shown) of the optical imaging system. The controller 530, memory 550, 3D scanner 545, wireless transceiver, and/or power source may also be housed within the housing. The optical imaging system 500 may also provide mechanisms to enable manual adjusting of the zoom optics 510 and/or focus optics 515. Such manual adjusting may be enabled in addition to motorized adjusting of zoom and focus.

The optical imaging system 500 may be mounted on a movable support structure, such as a positioning system (e.g. a robotic arm) of a navigation system, a manually operated support arm, a ceiling mounted support, a movable frame, or other such support structure. The optical imaging system 500 is removably mounted on the movable support structure. In some embodiments, the optical imaging system 500 may include a support connector, e.g. a mechanical coupling, to enable the optical imaging system 500 to be quickly and easily mounted or dismounted from the support structure. The support connector on the optical imaging system 500 may be suitable for connecting with a typical complementary connector on the support structure, e.g. as designed for typical end effectors. In some embodiments, the optical imaging system 500 may be mounted to the support structure together with other end effectors, or may be mounted to the support structure via another end effector.

When mounted, the optical imaging system 500 may be at a known fixed position and orientation relative to the support structure, by calibrating the position and orientation of the optical imaging system 500 after mounting. By determining the position and orientation of the support structure, e.g., using a navigation system or by tracking the movement of the support structure from a known starting point, the position and orientation of the optical imaging system 500 may also be determined. In some embodiments, the optical imaging system 500 may include a manual release button that when actuated, enables the optical imaging system 500 to be manually positioned.

In some embodiments, where the optical imaging system 500 is intended to be used in a navigation system environment, the optical imaging system 500 may include an array of trackable markers, which is mounted on a frame on the optical imaging system 500 to enable the navigation system to track the position and orientation of the optical imaging system 500. Alternatively, or additionally, the movable support structure, such as a positioning system of the navigation system, on which the optical imaging system 500 is mounted, may be tracked by the navigation system. The position and orientation of the optical imaging system 500 may be determined by using the known position and orientation of the optical imaging system 500 relative to the movable support structure.

The position and orientation of the optical imaging system 500 relative to a viewing target may be determined by a processor external to the optical imaging system 500, such as a processor of the navigation system. Information about the position and orientation of the optical imaging system 500 may be used, together with a robotic positioning system, to maintain alignment of the optical imaging system 500 with the viewing target throughout the medical procedure.

The navigation system tracks the position and orientation of the positioning system and/or the optical imaging system 500, either collectively or independently. The navigation system may determine the desired joint positions for the positioning system so as to maneuver the optical imaging system 500 to an appropriate position and orientation to maintain alignment with the viewing target. For example, the positioning system may be configured to align the longitudinal axes of the optical imaging system 500 and the access port. This alignment may be maintained throughout the medical procedure automatically, without requiring explicit control input. In some embodiments, the operator may be able to manually move the positioning system and/or the optical imaging system 500. During such manual movement, the navigation system may continue to track the position and orientation of the positioning system and/or the optical imaging system 500. After completion of manual movement, the navigation system may reposition and reorient the positioning system and the optical imaging system 500 to regain alignment with the access port.

The controller 530 may use information about the position and orientation of the optical imaging system 500 to perform auto-focusing. In particular, the controller 530 may be configured to perform auto-focusing operations for a camera of the optical imaging system 500. For example, the controller 530 may determine a working distance between the optical imaging system 500 and a viewing target, and based on the working distance, determine the desired positioning of the focus optics 515 to obtain a focused image. The position of the viewing target may, for example, be determined by a navigation system. The working distance may be determined by the controller 530 using information about the position and orientation of the optical imaging system 500 and/or the positioning system relative to the viewing target. In some embodiments, the working distance may be determined by the controller 530 using an infrared light (not shown) mounted on or near a distal end of the optical imaging system 500.

In some embodiments, the controller 530 may perform auto-focusing without reference to information about the position and orientation of the optical imaging system 500. For example, the controller 530 may adjust the focus actuator 525 to move the focus optics 515 into a range of focus positions and control the camera 535 to capture image data at each focus position. The controller 530 may then perform image processing on the captured images to determine which focus position has the sharpest image and determine that this focus position is the desired position of the focus optics 515. The controller 530 may then control the focus actuator 525 to move the focus optics 515 to the desired position. Other auto-focus routines, such as those suitable for handheld cameras, may be implemented by the controller 530 as appropriate.

A viewing target may be dynamically defined by an operator, for example, via touch input selecting a desired target on a touch-sensitive display, by using eye- or head-tracking to detect a point at which the operator's gaze is focused, and/or by voice command. The optical imaging system 500 may perform auto-focusing to dynamically focus the image on the defined viewing target, thereby enabling the operator to focus an image on different points within a field of view, without changing the field of view and without having to manually adjust the focus of the optical imaging system 500.

In at least some embodiments, the optical imaging system 500 may be configured to perform auto-focusing relative to a tracked tool, such as a medical instrument, that is used in a medical procedure. For example, the position and orientation of a medical instrument (e.g. a tracked pointer tool) may be determined, and the controller 530 may perform auto-focusing to focus the captured image on a point defined relative to the medical instrument. As the tracked tool is moved, the working distance between the optical imaging system 500 and a defined focus point of the tracked tool may change. The auto-focusing is performed in a manner similar to that as above described; however, instead of auto-focusing on a viewing target in the surgical field, the optical imaging system 500 focuses on a focus point that is defined relative to the tracked tool. The tracked tool may be used in the surgical field to guide the optical imaging system 500 to auto-focus on different points in the surgical field, enabling a surgeon to change the focus within a field of view, e.g. focus on a point other than at the center of the field of view, without changing the field of view and without needing to manually adjust the focus of the optical imaging system 500. Where the field of view includes objects at different depths, the surgeon may use the tracked tool, e.g. a pointer, to indicate to the optical imaging system 500 the object and/or depth desired for auto-focusing.

The controller 530 may receive information about the position and orientation of a medical instrument. This position and orientation information may be received, for example, from an external source, such as an external tracking system for tracking the medical instrument, or from another component of the optical imaging system 500, e.g. an infrared sensor or a machine vision component of the optical imaging system 500. The controller 530 may determine a focus point relative to the position and orientation of the medical instrument. The focus point may be predefined for a given medical instrument, e.g. the distal tip of a pointer, the distal end of a catheter, the distal end of an access port, the distal end of a soft tissue re-sector, the distal end of a suction, the target of a laser, or the distal tip of a scalpel), and is different for different medical instruments. The controller 530 may use this information, together with information about the known position and orientation of the optical imaging system 500 in order to determine the desired position of the focus optics 515 to achieve an image focused on the focus point defined relative to the medical instrument.

Where the optical imaging system 500 is used with a navigation system (such as the medical navigation system 205), the position and orientation of a medical instrument, e.g. tracked pointer tool 222, tracked port 210, etc. may be tracked and determined by the navigation system. The controller 530 of the optical imaging system 500 may automatically focus the optical imaging system 500 to a predetermined point relative to the tracked medical instrument. For example, the optical imaging system 500 may auto-focus on the tip of a tracked pointer tool or on the distal end of the access port 210.

Figure 4B:
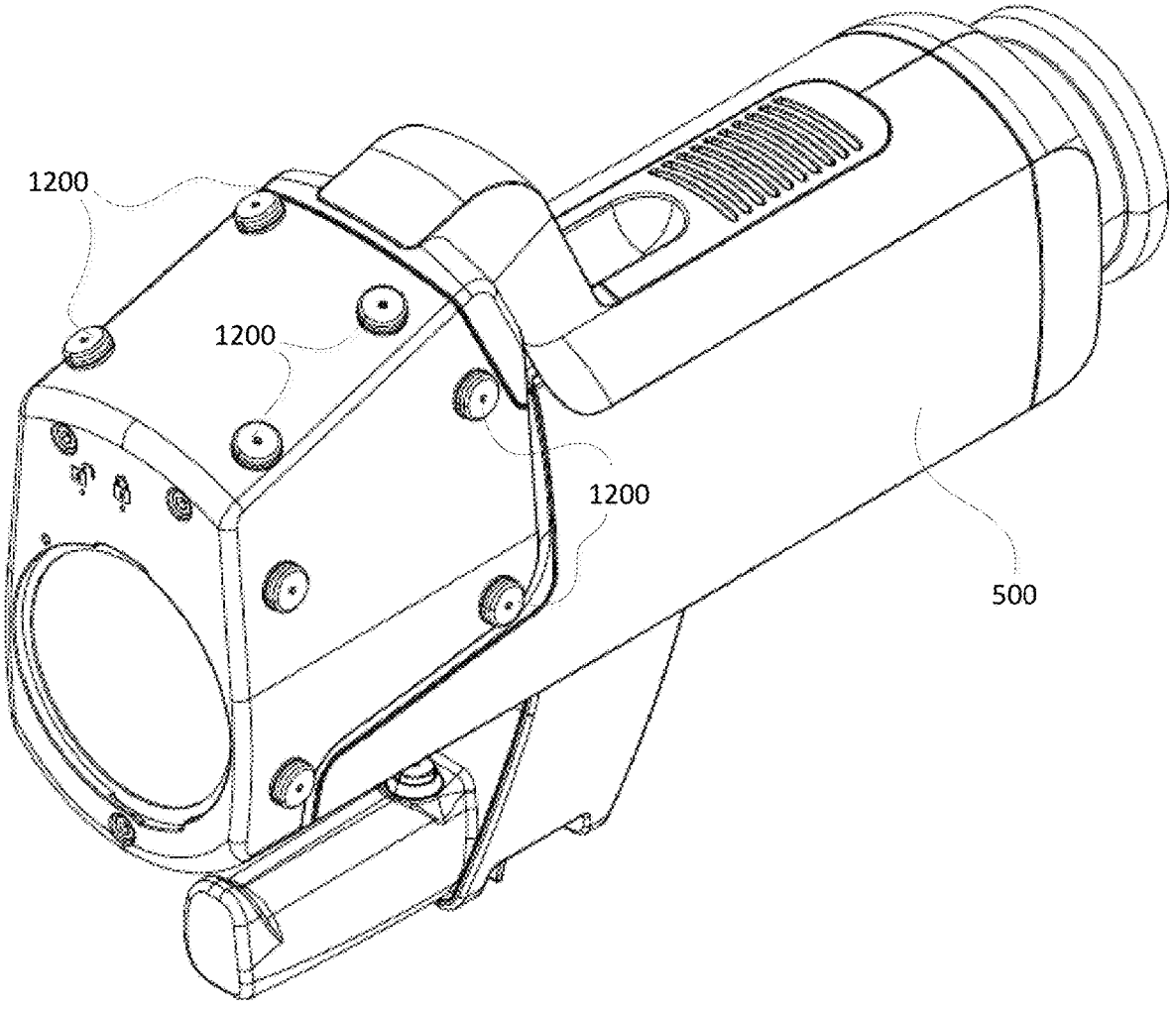
FIG. 4B is a perspective view of an example embodiment of an optical imaging system and a plurality of tracking markers.

FIG. 4B illustrates an example embodiment of an optical imaging system 500. Specifically, FIG. 4B is a perspective view of an end-effector which may house the components of the optical imaging system 500. The end-effector may be tracked, for example, using an external tracking system. As shown in FIG. 4B one or more tracking markers 1200 (e.g. spheres) may be coupled to the end-effector to facilitate tracking by a tracking system. The tracking system may include, at least, a stationary tracking camera 213 which detects the positions of the tracking markers 1200, enabling the tracking system to determine the position and orientation of the end-effector. The camera 535 of the optical imaging system 500 may be in a fixed position and/or orientation relative to the end-effectors tracking markers 1200. Accordingly, the position and orientation of the camera 535 may be tracked using the external tracking system. In particular, a distance between the camera 535 and a viewing target, such as a tracked medical instrument, may be obtained using the tracking system. That is, by tracking the position and/or orientation of a tracked medical instrument and the end-effector using tracking markers, an auto-focus driven focus distance of a camera of the optical imaging system 500 may be determined.

In at least some embodiments, the optical imaging system 500 may perform auto-focusing relative to a medical instrument only when the focus point relative to the medical instrument is determined to be within the field of view of the optical imaging system 500. Where the optical imaging system 500 is mounted on a movable support system, such as a robotic arm, if the focus point of the medical instrument is outside of the current field of view of the optical imaging system 500, the movable support system may position and orient the optical imaging system 500 to bring the focus point of the medical instrument within the field of view of the optical imaging system 500, in response to input such as a voice command, activation of a foot pedal, etc.

The optical imaging system 500 may implement a time lag before performing auto-focus relative to a medical instrument, in order to avoid erroneously changing focus while the focus point of the medical instrument is brought into, and out of, the field of view. For example, the optical imaging system 500 may be configured to auto-focus on a focus point of a tracked medical instrument only after the focus point has been substantially stationary for a predetermined length of time, e.g. approximately 0.5 second to 1 second. In some embodiments, the optical imaging system 500 may also be configured to perform zooming with the focus point as the zoom center. For example, while a focus point is in the field of view, or after auto-focusing on a certain point in the field of view, the user may provide command input to instruct the optical imaging system 500 to zoom in on the focus point. The controller 530 may then position the zoom optics 520 accordingly to zoom in on the focus point. Where appropriate, the positioning system may automatically reposition the optical imaging system 500 as needed to center the zoomed in view on the focus point.

In some embodiments, the optical imaging system 500 may automatically change between different auto-focus modes. For example, if the current field of view does not include any focus point defined by a medical instrument, the controller 530 may perform auto-focus based on preset criteria, e.g. to obtain the sharpest image or to focus on the center of the field of view. When a focus point defined by a medical instrument is brought into the field of view, the controller 530 may automatically switch mode to auto-focus on the focus point. In some embodiments, the optical imaging system 500 may change between different auto-focus modes in response to user input. In particular, a user may trigger auto-focus (e.g. single or continuous auto-focus) in the optical imaging system 500 via, for example, user command on a user interface, voice input, or activation of a foot pedal (e.g. button press, acknowledgement, etc.). In various examples of auto-focusing, whether or not relative to a medical instrument, the optical imaging system 500 may be configured to maintain the focus as the zoom is adjusted.

The optical imaging system 500 may additionally generate a depth map (not shown). This is performed by capturing images of the same field of view, wherein the optical imaging system 500 focuses on points at a plurality of different depths to simulate 3-D depth perception. For example, the optical imaging system 500 may perform auto-focusing through a predefined depth range, through a depth of approximately 1 centimeter, and capturing focused images at a plurality of different depths through a depth range. The plurality of images captured at the corresponding different depths may be transmitted to an external system, such as an image viewing workstation, and the plurality of images may be aggregated into a set of depth images to form a depth map for the same field of view.

The presently disclosed methods for performing auto-focus operations are described with reference to FIGS. 6 and 7. More specifically, the methods 600 and 700 illustrated in FIGS. 6 and 7, respectively, may enable recovery of focus in a continuous auto-focus mode for an optical imaging system. In a medical procedure, an optical imaging system (i.e. a camera of the optical imaging system) may automatically focus on a focus point defined relative to a tracked medical instrument, such as a pointer tool. When the tracked medical instrument is removed from a field of view of the camera, out-of-focus images may be produced by the camera. In particular, a focus distance of the camera may be set to random values as the tracked medical instrument is moved out of the field of view of the camera.

Figure 8A:
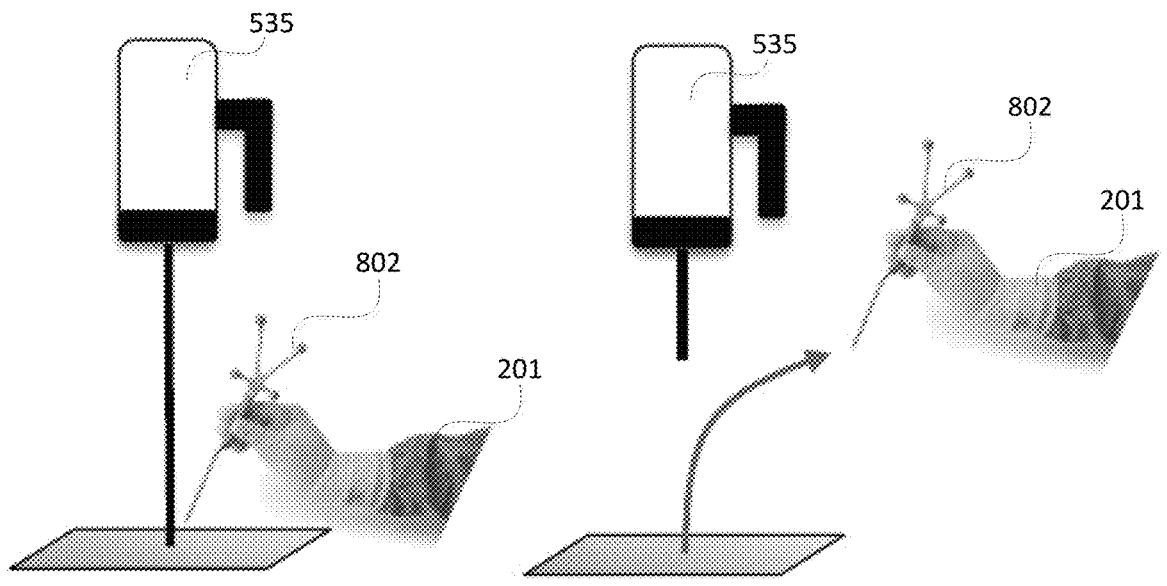
FIGS. 8A-8B illustrate the effects on focus distance of a camera which result from movement of a tracked viewing target.

This scenario is illustrated in FIG. 8A. The surgeon 201 may use a tracked medical instrument 802 during a procedure, and the camera 535 may be configured to auto-focus on a defined focus point relative to the tracked medical instrument 802. By virtue of the auto-focusing, the surgeon 201 may be able to observe a surgical site of interest when the tracked medical instrument 802 is moved over, or in proximity to, the surgical site. However, if the surgeon 201 removes the tracked medical instrument 802 from a field of view of the camera 535, the camera 535 may produce an out-of-focus image. This loss of focus may, at least temporarily, impede the surgeon 201 from observing the surgical site with the desired zoom and focus using the camera 535.

Figure 8B:
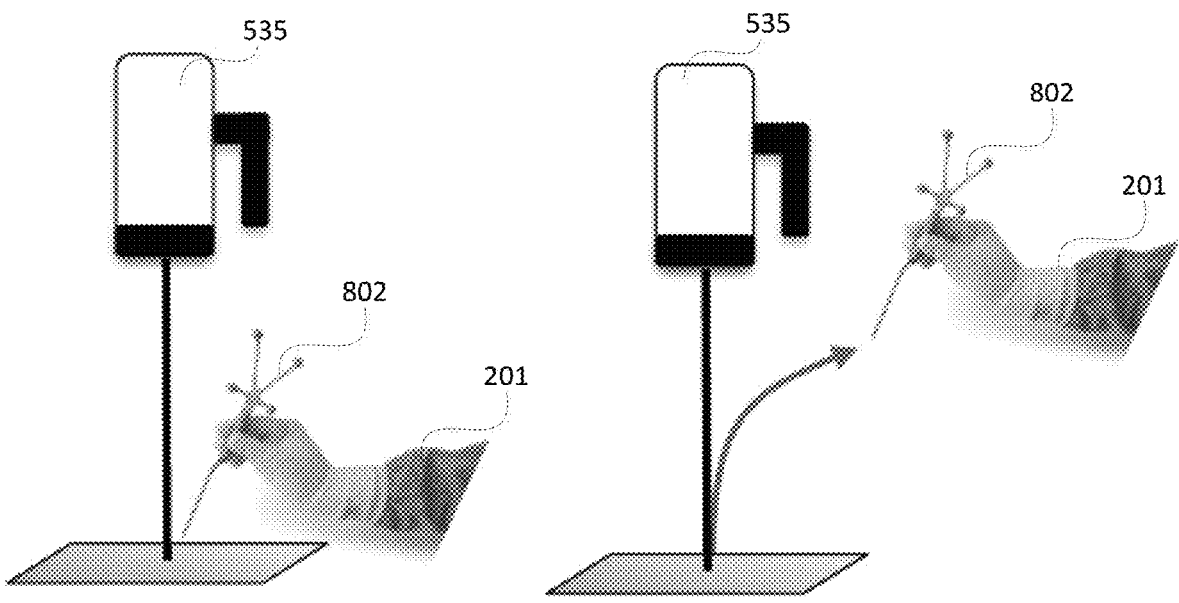

A desired auto-focus scenario is illustrated in FIG. 8B. In FIG. 8B, as the surgeon 201 removes the tracked medical instrument 802 from the field of view of the camera 535, the focus of the camera 535 may change until the tracked medical instrument is completely outside of the field of view of the camera 535. The focus distance of the camera 535 can then be returned to a most recent focus distance value that was set with intent, for example, by the surgeon 201. In particular, the focus distance of the camera 535 may, after a period of fluctuation during removal of the tracked medical instrument from the field of view of the camera 535, be set to the most recent value of focus distance that was determined to be stable prior to the removal from the field of view of the camera 535.

Figure 6:
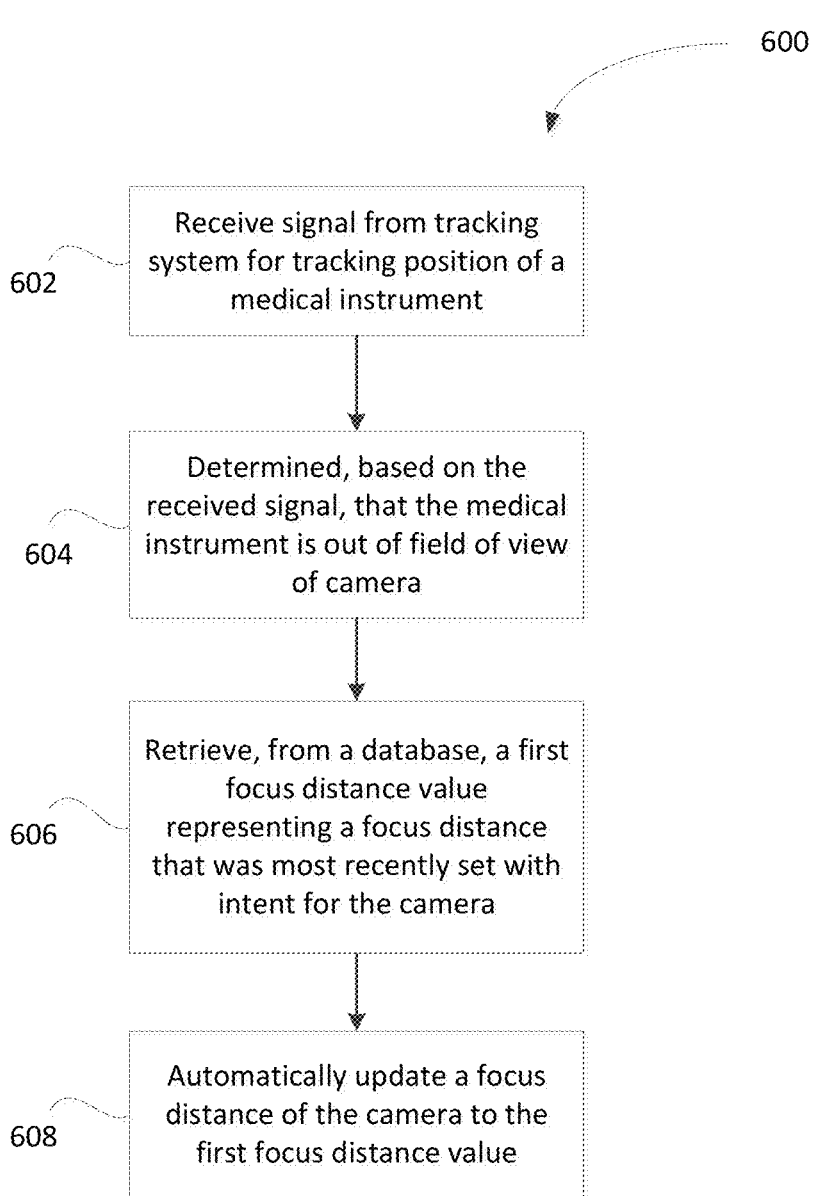
FIG. 6 shows, in flowchart form, an example method for performing auto-focus in a camera of the optical imaging system of FIG. 5.

FIG. 6 shows, in flowchart form, an example method 600 for recovering auto-focus in a camera of an optical imaging system. The method 600 may be implemented in a digital microscope system. For example, the method 600 may be implemented by a controller of an optical imaging system integrated into a digital microscope, or similar processing unit for controlling operations of a camera of an optical imaging system. The optical imaging system is configured for continuous auto-focusing. In particular, the camera is configured to automatically focus to a defined focus point relative to a tracked tool, such as a medical instrument.

In operation 602, the controller receives a signal from a tracking system for tracking a position of a medical instrument. The signal represents an indication of, at least, a position of the medical instrument relative to the camera of the optical imaging system. In particular, the signal may include a representation of the position of a defined point of the medical instrument with respect to a field of view of the camera. The tracking system may be configured to track a point (e.g. a distal tip) defined relative to the medical instrument, and the signal may indicate the position of this defined point with respect to the field of view of the camera. In some embodiments, the signal may additionally represent an orientation of the medical instrument relative to the camera. For example, the signal may include a representation of an orientation of a defined portion of the medical instrument with respect to a field of view of the camera.

In operation 604, the controller determines, based on the received signal, that the medical instrument is removed from a field of view of the camera. For example, the controller may determine that a defined point on the medical instrument is positioned outside of the field of view of the camera. In some embodiments, the controller may detect an approximate speed of the medical instrument and determine whether the medical instrument is being removed from the field of view of the camera based on the speed data. For example, the tracking system may be configured to detect an approximate speed of a defined point on the medical instrument and transmit the speed data to the controller at certain intervals. Based on the received speed data, if the approximate speed of (a defined point on) the medical instrument exceeds a predefined threshold speed, the controller may determine that the medical instrument is being removed from the field of view of the camera. Alternatively, the speed data may be obtained via a finite difference computation, as will be described in greater detail below.

If the auto-focus mode is enabled for the camera, the controller may, upon determining that the medical instrument is removed from the field of view of the camera, adjust a focus distance of the camera. This behavior may be desirable in the continuous auto-focus mode in order to ensure that the latest stable focus position is recovered and the focus continues to track to the surgical site. Thus, in operation 606, the controller retrieves, from a database, a first focus distance value representing a focus distance that was most recently set with intent for the camera. The database may, in some embodiments, be a rolling buffer containing recent focus distance data for the camera. For example, the rolling buffer may store a predetermined number of most recent auto-focus driven focus distance values for the camera and timestamps associated with the detected focus distance values. The focus distance values may be obtained, for example, from the camera or determined by the controller itself.

The retrieved first focus distance may be a value of focus distance stored in the database with the most recent timestamp. The focus distance values that are stored in the database may represent, for example, stable focus distances, or focus distances corresponding to in-focus imaging by the camera. The stable focus distances may, in some embodiments, be associated with dwell periods which last longer than a predefined threshold. A dwell period refers to a period of time during which a tracked medical instrument "dwells" or remains in relatively fixed distance with respect to the camera. A longer dwell period may represent steady or stable positioning of the medical instrument relative to the camera, whereas a short dwell period may correlate to movement of the medical instrument. The controller (or the camera itself) may store those focus distance values that are determined to be stable based, for example, on dwell periods.

In operation 608, the controller automatically updates a focus distance of the camera to the retrieved first focus distance value. That is, the focus distance of the camera may be automatically set to the first focus distance value determined by the controller, and not a different focus distance value which may result from the default auto-focus behavior for the tracked medical instrument.

FIG. 7 shows, in flowchart form, another example method 700 for recovering auto-focus in a camera of an optical imaging system. As for the method 600, the method 700 may be implemented in a digital microscope system. For example, the method 700 may be implemented by a controller of an optical imaging system integrated into a digital microscope, or similar processing unit for controlling operations of a camera of an optical imaging system. The optical imaging system is configured for continuous auto-focusing. In particular, the camera is configured to automatically focus to a defined focus point relative to a tracked tool, such as a medical instrument.

The method 700 employs a speed-based approach to determining a stable focus distance value when recovering continuous auto-focusing for a camera. In particular, the method is based on an assumption that a focus distance that is set with intent by an operator of the camera will have an associated dwell period during which a tracked tool driven focus distance has an associated speed that is consistently below a predefined threshold. That is, a stable focus distance value may correspond to a period of time during which a tracked tool is moved at a speed that is less than a threshold. The continuous auto-focus of the camera may be recovered by automatically setting a focus distance of the camera to the most recent such stable focus distance value.

In operation 702, the controller stores focus distance values and associated timestamps for the camera in a database. The database may, for example, be a rolling buffer for storing a predetermined number of most recent focus distance values for the camera.

The controller detects, in operation 704, that a tracked medical instrument is out of field of view of the camera. For example, the controller may receive, from a tracking system for tracking the medical instrument, a signal representing an indication of the position and/or orientation of the medical instrument relative to the camera. Based on the received signal, the controller may determine whether the medical instrument is out of, or being removed from, the field of view of the camera. For example, the controller may compare coordinates associated with the camera's field of view with coordinates of the medical instrument (or a defined point relative to the medical instrument) in the same coordinate space. Upon comparing the coordinates, the controller may be able to determine whether the medical instrument is within, or falls outside of, the bounds of the camera's field of view.

In operation 706, the controller obtains, for each stored focus distance value, an associated speed value. The speed values represent the instantaneous speeds of the tracked medical instrument at the respective focus distances. That is, the associated speed value represents an approximate speed of a tracked point of the medical instrument at the focus distance. In at least some embodiments, the associated speed for a focus distance value may be approximated numerically. For example, the associated speed may be obtained based on a finite difference computation using stored focus distance values for the camera. That is, the rates at which the focus distance values change, presumably as a result of movement of the tracked medical instrument, may be approximated. Various techniques for computing finite difference approximations may be suitable. In some embodiments, the calculation of weights in finite difference formulas during the calculation of approximate speeds may be based on an approach proposed in "Calculation of Weights in Finite Difference Formulas" (Fornberg, SIAM Rev. vol, 40, no. 3, pp. 685-691, September 1998), which is incorporated herein by reference. The controller may additionally, or alternatively, be configured to compute a speed curve associated with the stored focus distance values. In particular, a speed curve representing approximate speeds of the medical instrument which are associated with the stored focus distance values may be computed. Such speed curve may facilitate identification of focus distance values that are "stable", or associated with dwell periods during which the associated speed falls below a given threshold.

The speed values that are approximated numerically may be stored in association with the respective focus distance values. In operation 708, the controller retrieves a first focus distance value that is associated with a speed which is below a predefined threshold speed. In particular, the controller retrieves the most recent such focus distance value. In some embodiments, the predefined threshold speed may be 0.1 meter per second. The controller may retrieve from a data buffer the focus distance value with the most recent time-stamp and which is associated with a speed that falls below the predefined threshold.

Upon retrieving the first focus distance value, the controller automatically updates a focus distance of the camera to the retrieved value, in operation 710. That is, the focus distance of the camera may be automatically set to the first focus distance value in order to recover continuous auto-focus and for the focus to track to the surgical site.

The various embodiments presented above are merely examples and are in no way meant to limit the scope of this application. Variations of the innovations described herein will be apparent to persons of ordinary skill in the art, such variations being within the intended scope of the present application. In particular, features from one or more of the above-described example embodiments may be selected to create alternative example embodiments including a sub-combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A processor-implemented method for performing auto-focus in a camera, the method comprising:
storing a plurality of focus distance values and associated speed values based on tracked movement of a medical instrument in a field of view of the camera;
receiving a first user input for triggering a change between a plurality of auto-focus modes; and
in response to receiving the first user input:
determining that a focus point defined by the medical instrument is within the field of view of the camera;
automatically selecting one of the previously stored focus distance values having an associated speed value that is below a predefined threshold; and
performing a single auto-focus operation for focusing by updating a focus distance of the camera to the selected previously stored focus distance.

2. The method of claim 1, further comprising:
determining that a continuous auto-focus mode for the camera is enabled prior to receiving the first user input,
wherein performing the single auto-focus operation comprises switching from the continuous auto-focus mode to a single auto-focus mode.

3. The method of claim 1, wherein the first user input comprises input on a user interface.

4. The method of claim 1, wherein the first user input comprises voice command.

5. The method of claim 1, wherein the first user input comprises confirmation input for activation of a foot pedal.

6. The method of claim 1, further comprising:
receiving a second user input for enabling a continuous auto-focus mode for the camera; and
in response to receiving the second user input, causing the camera to switch from the single auto-focus mode to the continuous auto-focus mode.

7. A navigation system to support a medical procedure, the navigation system comprising:

a tracking system for tracking a position of a medical instrument;
a surgical camera for imaging a target surgical site; and
a processor coupled to the tracking system and the surgical camera, the processor being configured to:
store a plurality of focus distance values and associated speed values based on tracked movement of the medical instrument in a field of view of the surgical camera;
receive a first user input for triggering a change between a plurality of auto-focus modes; and
in response to receiving the first user input:
determine that a focus point defined by the medical instrument is within the field of view of the camera;
automatically select one of the previously stored focus distance values having an associated speed value that is below a predefined threshold; and
perform a single auto-focus operation for focusing by updating a focus distance of the camera to the selected previously stored focus distance.

8. The navigation system of claim 7, wherein the processor is further configured to:
determine that a continuous auto-focus mode for the camera is enabled prior to receiving the first user input,
wherein performing the single auto-focus operation comprises switching from the continuous auto-focus mode to a single auto-focus mode.

9. The navigation system of claim 7, wherein the first user input comprises input on a user interface.

10. The navigation system of claim 7, wherein the first user input comprises voice command.

11. The navigation system of claim 7, wherein the first user input comprises confirmation input for activation of a foot pedal.

12. The navigation system of claim 7, wherein the processor is further configured to:
receive a second user input for enabling a continuous auto-focus mode for the camera; and
in response to receiving the second user input, cause the camera to switch from the single auto-focus mode to the continuous auto-focus mode.

13. A non-transitory processor-readable storage medium storing processor-executable instructions that, when executed by a processor, are to cause the processor to:
store a plurality of focus distance values and associated speed values based on tracked movement of a medical instrument in a field of view of a camera;
receive a first user input for triggering a change between a plurality of auto-focus modes; and
in response to receiving the first user input:
determine that a focus point defined by the medical instrument is within the field of view of the camera;
automatically select one of the previously stored focus distance values having an associated speed value that is below a predefined threshold; and
perform a single auto-focus operation for focusing by updating a focus distance of the camera to the selected previously stored focus distance.

14. The non-transitory processor-readable storage medium of claim 13, wherein the instructions, when executed, are to further cause the processor to:
determine that a continuous auto-focus mode for the camera is enabled prior to receiving the first user input,
wherein performing the single auto-focus operation comprises switching from the continuous auto-focus mode to a single auto-focus mode.

15. The non-transitory processor-readable storage medium of claim 13, wherein the first user input comprises confirmation input for activation of a foot pedal.

16. The non-transitory processor-readable storage medium of claim 13, wherein the first user input comprises voice command.

17. The non-transitory processor-readable storage medium of claim 13, wherein the instructions, when executed, are to further cause the processor to:

receive a second user input for enabling a continuous auto-focus mode for the camera; and in response to receiving the second user input, cause the camera to switch from the single auto-focus mode to the continuous auto-focus mode.

18. The method of claim 1, wherein the predefined threshold speed is 0.1 meters per second.

19. The system of claim 7, wherein the predefined threshold speed is 0.1 meters per second.

20. The non-transitory processor-readable storage medium of claim 13, wherein the predefined threshold speed is 0.1 meters per second.

\* \* \* \* \*